United States Patent
Baker, Jr.

(10) Patent No.: US 9,801,584 B2
(45) Date of Patent: Oct. 31, 2017

(54) METHOD FOR DETECTION OF ABERRANT TISSUE SPECTRA

(75) Inventor: Clark R. Baker, Jr., Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 950 days.

(21) Appl. No.: 13/598,312

(22) Filed: Aug. 29, 2012

(65) Prior Publication Data

US 2012/0323095 A1 Dec. 20, 2012

Related U.S. Application Data (62) Division of application No. 11/716,777, filed on Mar. 9, 2007, now Pat. No. 8,280,469.

(51) Int. Cl.
*A61B 5/1455* (2006.01)
*A61B 5/00* (2006.01)

(52) U.S. Cl.
CPC ........ *A61B 5/6843* (2013.01); *A61B 5/14551* (2013.01); *A61B 5/7203* (2013.01); *A61B 5/14552* (2013.01)

(58) Field of Classification Search
CPC . A61B 5/0205; A61B 5/1455; A61B 5/14551; A61B 5/14552; A61B 5/72; A61B 5/7203
USPC ....... 600/310, 322, 323, 324, 326, 331, 336, 600/340, 473, 476; 356/41
See application file for complete search history.

(56) References Cited

U.S. PATENT DOCUMENTS

| | | | |
|---|---|---|---|
| 33,643 A | 7/1991 | Isaacson et al. | |
| 5,638,816 A * | 6/1997 | Kiani-Azarbayjany et al. | 600/316 |
| 5,995,856 A * | 11/1999 | Mannheimer et al. | 600/322 |
| 6,173,196 B1 | 1/2001 | Delonzor et al. | |
| 6,388,240 B2 | 5/2002 | Schulz et al. | |
| 6,430,423 B2 | 8/2002 | DeLonzor et al. | |
| 6,580,086 B1 | 6/2003 | Schulz et al. | |
| 6,591,122 B2 * | 7/2003 | Schmitt | 600/310 |
| 6,628,975 B1 * | 9/2003 | Fein et al. | 600/323 |
| 6,694,160 B2 | 2/2004 | Chin | |
| 6,763,255 B2 | 7/2004 | DeLonzor et al. | |
| 6,813,511 B2 | 11/2004 | Diab et al. | |
| 7,190,984 B1 | 3/2007 | DeLonzor et al. | |
| 7,190,985 B2 | 3/2007 | Petersen et al. | |
| 7,321,790 B2 | 1/2008 | DeLonzor et al. | |
| 7,369,886 B2 | 5/2008 | DeLonzor et al. | |
| 7,373,188 B2 | 5/2008 | DeLonzor et al. | |
| 7,373,189 B2 | 5/2008 | Delonzor et al. | |
| 7,373,190 B2 | 5/2008 | Delonzor et al. | |

(Continued)

*Primary Examiner* — Eric Winakur
*Assistant Examiner* — Chu Chuan (JJ) Liu
(74) *Attorney, Agent, or Firm* — Fletcher Yoder PC (57) ABSTRACT

A method is provided for determining contact of a sensor with a patient's tissue. The method comprises comparing the intensity of detected light at a first wavelength to a threshold, wherein the first wavelength is not used to determine a physiological characteristic of the patient, and determining if the sensor is in contact with the patient's tissue based on the comparison. In addition, a method is provided for determining the amount of light shunting during operation of the sensor. The method comprises comparing the intensity of detected light at a first wavelength to a threshold, wherein the first wavelength is not used to determine a physiological characteristic of the patient, and determining the amount of light shunting based on the comparison.

20 Claims, 5 Drawing Sheets

(56) References Cited

U.S. PATENT DOCUMENTS

| | | |
|---|---|---|
| 7,373,191 B2 | 5/2008 | DeLonzor et al. |
| 7,386,334 B2 | 6/2008 | DeLonzor et al. |
| 7,389,130 B2 | 6/2008 | Delonzor et al. |
| 7,400,919 B2 | 7/2008 | Petersen et al. |
| 7,418,284 B2 | 8/2008 | DeLonzor et al. |
| 2007/0021659 A1 | 1/2007 | DeLonzor et al. |
| 2007/0021660 A1 | 1/2007 | DeLonzor et al. |
| 2007/0021662 A1 | 1/2007 | DeLonzor et al. |
| 2007/0027378 A1 | 2/2007 | DeLonzor et al. |
| 2007/0027379 A1 | 2/2007 | Delonzor et al. |
| 2007/0027380 A1 | 2/2007 | DeLonzar et al. |
| 2007/0073117 A1 | 3/2007 | Raridan, Jr. |
| 2007/0129616 A1 | 6/2007 | Rantala |
| 2008/0076982 A1 | 3/2008 | Oilerdessen et al. |
| 2008/0197301 A1 | 8/2008 | Diab |
| 2008/0221427 A1 | 9/2008 | Petersen |

* cited by examiner

METHOD FOR DETECTION OF ABERRANT TISSUE SPECTRA

CROSS-REFERENCE TO RELATED APPLICATIONS

This application is a divisional of U.S. patent application Ser. No. 11/716,777, entitled "Method for Detection of Aberrant Tissue Spectra," filed Mar. 9, 2007, which is herein incorporated by reference in its entirety.

BACKGROUND OF THE INVENTION

1. Field of the Invention

The present invention relates generally to medical devices and, more particularly, to the determination of placement of a medical device.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. For example, to measure certain characteristics, a non-invasive sensor may be utilized that transmits electromagnetic radiation, such as light, through a patient's tissue and then photo-electrically detects the absorption and scattering of the transmitted or reflected light in such tissue. The physiological characteristics of interest may then be calculated based upon the amount of light absorbed and/or scattered or based upon changes in the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue. In this manner, the measured amount of light absorbed and/or scattered may then be used to estimate the amount of blood or tissue constituent in the tissue using various algorithms.

One technique for monitoring the physiological characteristics of a patient is commonly referred to as pulse oximetry, and devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsation supplying the tissue, and/or the rate of blood pulsations corresponding to each heart beat of a patient. Such physiological information allows doctors and other health care personnel to provide the best possible health care for their patients.

In processing a signal received by a pulse oximeter sensor, or any other non-invasive sensor utilizing similar data acquisition principles, the quality of the signal is typically dependent on the sensor making proper contact with the tissue. The sensor may be misplaced on the patient, or jostled or bumped, thereby affecting the contact of the sensor with the patient's tissue. In such instances, or in other circumstances where there may be poor contact between the sensor and the skin, light that otherwise might provide useful information may escape to the environment and never be detected or it may reach the light detection mechanism without passing through the patient's tissue, effectively providing no physiological information while reducing signal quality. Such lost or degraded information regarding the physiological characteristic, such as blood oxygen saturation, may result in an inaccurate indication of the patient's condition being provided to a health care provider.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for determining contact of a sensor with a patient's tissue that includes: emitting light at three or more wavelengths into a patient's tissue, wherein the three or more wavelengths includes a first wavelength that is not used to determine a physiological characteristic of the patient light; detecting the light; comparing the intensity of the detected light at the first wavelength to a threshold; and determining if the sensor is in contact with the patient's tissue based on the comparison.

There is also provided a method for correcting light shunting that includes: emitting light at three or more wavelengths into a patient's tissue, wherein the three or more wavelengths includes a first wavelength that is not used to determine a physiological characteristic of the patient light; detecting the light with at least one detector disposed on the sensor body; comparing the intensity of the detected light at the third wavelength to a threshold; and determining the amount of light shunting between the at least one emitter and the at least one detector based on the comparison.

A monitor is provided. The monitor includes: an I/O port configured to connect a sensor; and a processor configured to execute an algorithm configured to compare a wavelength of detected light to a threshold, wherein the wavelength is not used to determine a physiological characteristic of the patient, and an algorithm configured to determine if a sensor is in contact with the patient's tissue based on the comparison.

A sensor is provided. The sensor includes: one or more light emitting components configured to emit light at three or more wavelengths, wherein at least one of the wavelengths is not used to determine a physiological characteristic but is used to determine the sufficiency of contact between the sensor and the tissue of a patient; one or more light detecting components configured to detect the light emitted by the one or more light emitting components; and a sensor body upon which the one or more light emitting components and the one or more light detecting components are disposed A sensor assembly is provided. The sensor assembly includes: a sensor body;
an emitter configured to emit light at three or more wavelengths into a patient's tissue; a detector configured to detect the light; and a monitor configured to execute an algorithm configured to compare a wavelength of detected light to a threshold, wherein the wavelength is not used to determine a physiological characteristic of the patient, and an algorithm configured to determine if a sensor is in contact with the patient's tissue based on the comparison.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a method for determining if a sensor, such as for use in pulse oximetry or other applications utilizing spectrophotometry, is in contact with a patient's tissue. Further, it is also desirable to provide a method for estimating the amount of light shunting in such a sensor and to use the estimated amount of light shunting to correct sensor measurements. In accordance with some aspects of the present technique, a patient sensor and monitor are provided that are configured to determine if the sensor is in suitable contact with the patient's tissue. If the sensor is not in suitable contact, a notification may be provided to a clinician or operator, allowing the clinician or operator to correct the lack of suitable contact.

Figure 1:
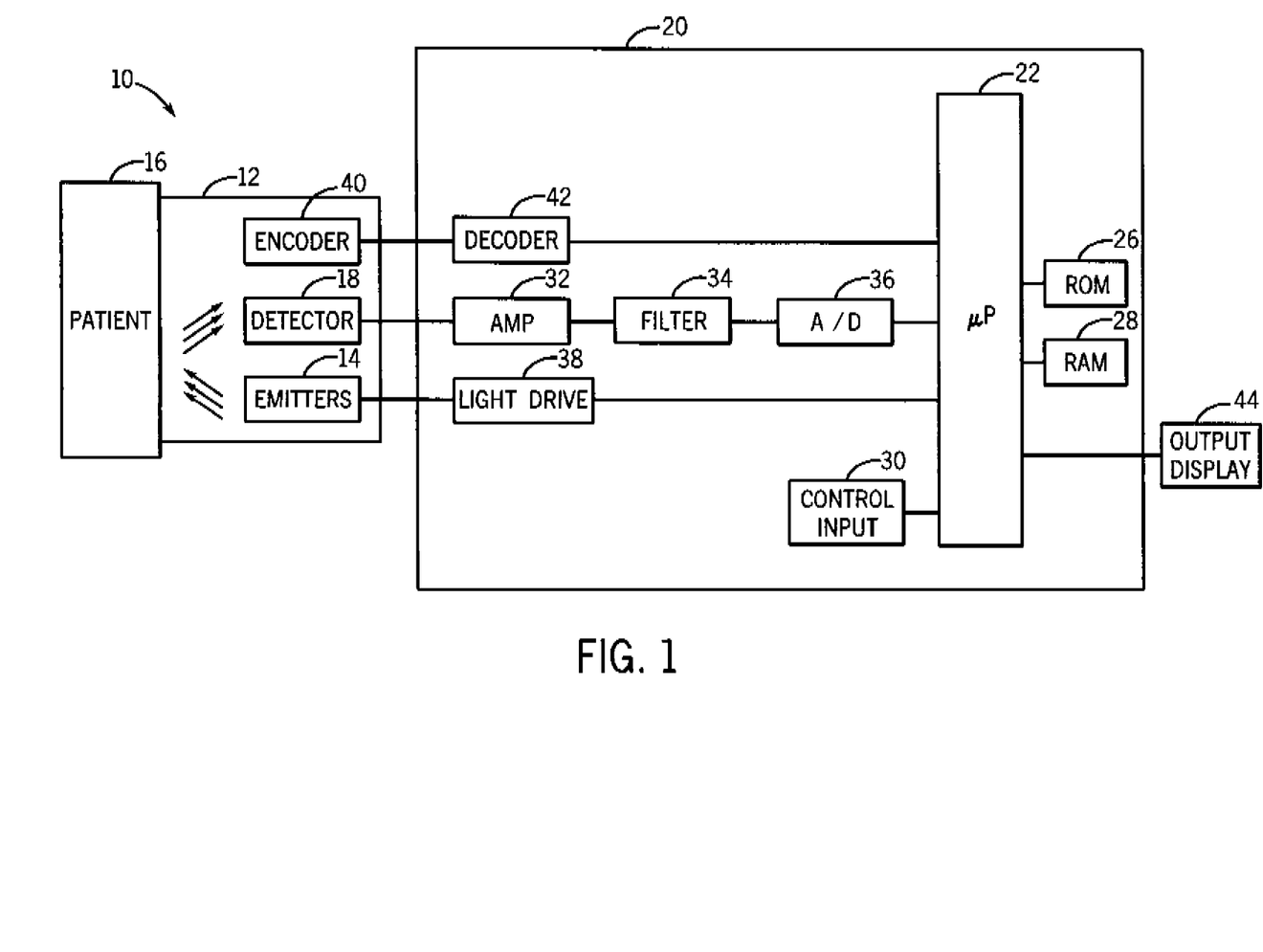
FIG. 1 illustrates a block diagram of a sensor and patient monitoring system in accordance with an exemplary embodiment of the present invention.

Prior to discussing the present technique in detail, it should be appreciated that exemplary acts of the present technique are typically implemented in a patient monitoring system including a sensor for attachment to a patient. For example, FIG. 1 illustrates a block diagram of a sensor and patient monitoring system 10 in accordance with an exemplary embodiment of the present approach. The system 10 is exemplary and an actual implementation may include more or fewer components as needed for a specific application for which the system 10 is to be used, such as for pulse oximetry applications. The system 10 includes a sensor assembly 12 for attachment to a patient 16. In an exemplary embodiment, the sensor assembly 12 includes an emitter 14 configured to emit electromagnetic radiation, such as light, into the tissue of the patient 16. The electromagnetic radiation is scattered and/or absorbed by the various constituents of the patient's blood and/or tissues. A photoelectric detector 18 in the sensor 12 is configured to detect the scattered and/or reflected light and to generate a corresponding electrical signal. In the depicted exemplary embodiment, the electrical signal is provided to a spectrophotometric monitor 20, such as a pulse oximetry or multi-parameter monitor, such as those available from Nellcor Puritan Bennett, Inc.

In the depicted embodiment, the spectrophotometric device or patient monitor 20 has a microprocessor 22 which calculates various patient parameters, characteristics, and/or other metrics using algorithms programmed into the monitor 20. The microprocessor 22 is connected to other component parts of the monitor 20, such as a ROM 26, a RAM 28, and control inputs 30. In certain embodiments, the ROM 26 holds the algorithms used to compute the patient parameters, characteristics, and/or metrics. The RAM 28 stores the values detected by the detector 18 for use in the algorithms.

In some embodiments, one or more control inputs 30 allow a user to interface with the spectrophotometric monitor 20. Patient data may be entered, such as gender, weight, age and medical history data. This information may be used to validate the baseline measurements or to assist in the understanding of anomalous readings. The control inputs 30 may include soft keys, dedicated function keys, keyboard, and/or keypad type interfaces for providing parameters, data or instructions to the monitor 20. In certain embodiments, the control input 30 may also include speech or tone recognition or other audio command input type devices.

Signals are passed from the sensor 12 to the spectrophotometric monitor 20 for processing. In one embodiment, the signals are amplified and filtered by amplifier 32 and filter 34, respectively, before being converted to digital signals by an analog-to-digital converter 36. The signals may then be used to determine the patient parameters, characteristics, and/or metrics and/or stored in RAM 28.

A light drive unit 38 in the spectrophotometric monitor 20 controls the timing of the emitters 14. While the emitters 14 are manufactured to operate at one or more certain wavelengths, variances in the wavelengths actually emitted may occur which may result in inaccurate readings. To help avoid inaccurate readings, an encoder 40 and decoder 42 may be used to calibrate the spectrophotometric monitor 20 to the actual wavelengths emitted by the emitters 14. The encoder 40 may be a resistor, for example, whose value corresponds to coefficients stored in the spectrophotometric device 20. The coefficients may then be used in the algorithms. Alternatively, the encoder 40 may also be a memory device, such as an EPROM, that stores information, such as the coefficients themselves. Once the coefficients are determined by the spectrophotometric monitor 20, they are inserted into the algorithms in order to calibrate the system 10.

The spectrophotometric monitor 20 may be configured to display the calculated values, such as blood oxygen saturation, tissue hydration, and so forth, on display 44. The display 44 may show the calculated values numerically and/or as a waveform over time. Additionally, any notifications or alerts prompted by abnormal measurements or calculated values or by poor contact between the sensor and the patient's tissue, as discussed below, may be displayed on the display 44.

Figure 2:
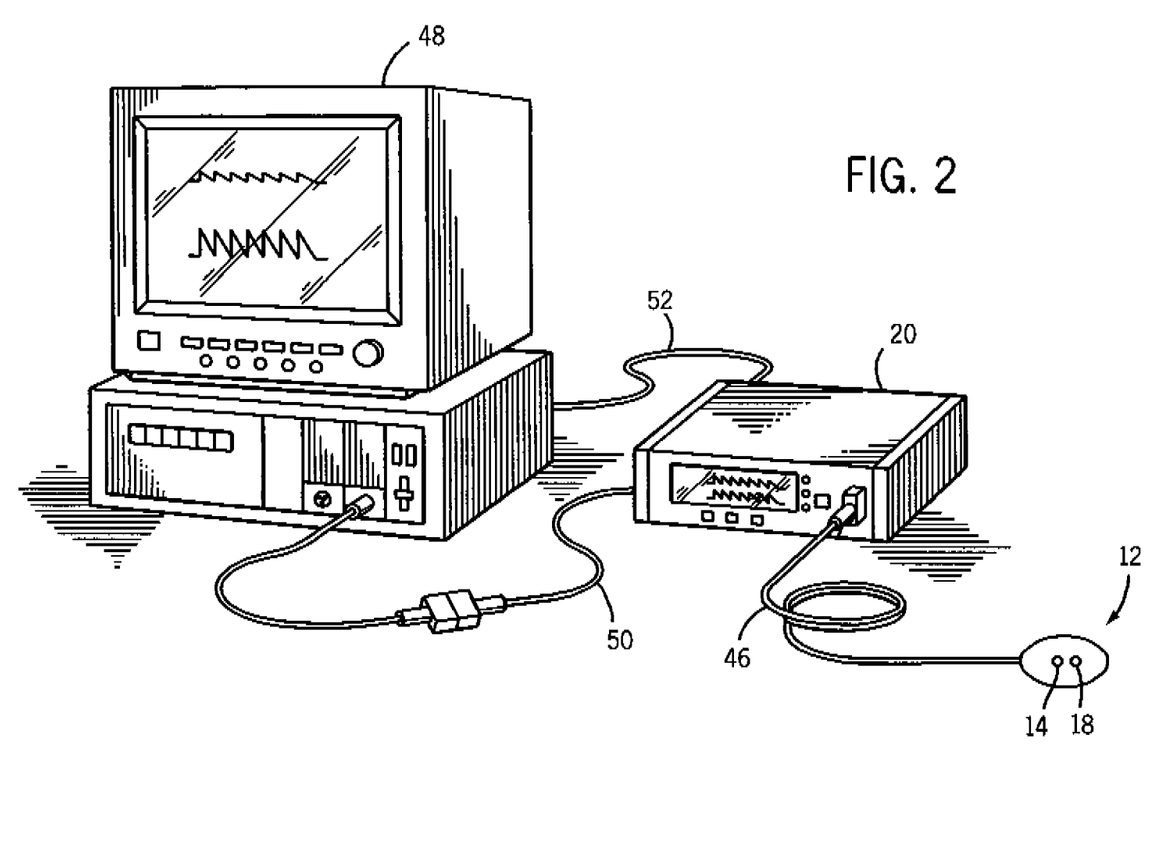
FIG. 2 illustrates a patient monitoring system coupled to a multi-parameter patient monitor and a reflectance-type forehead sensor, in accordance with aspects of the present technique.

Referring now to FIG. 2, the sensor 12, which may be a pulse oximetry or other spectrophotometric sensor such as a spectrophotometric sensor available from Nellcor Puritan Bennett, Inc., is shown as an exemplary reflectance-type forehead sensor for use in conjunction with a patient monitor 20. In the depicted embodiment, a sensor cable 46 connects the sensor 12 to the patient monitor 20. As will be appreciated by those of ordinary skill in the art, the sensor 12 and/or the sensor cable 46 may include or incorporate one or more integrated circuit devices or electrical devices, such as a memory, processor chip, or resistor, that may facilitate or enhance communication between the sensor 12 and the patient monitor 20. For example, as described above, the sensor 12 or the cable 46 may include an encoder 40 for storing values or identifying information which may be used by the monitor 20 in operation. Likewise the sensor cable 46 may be an adaptor cable, with or without an integrated circuit or electrical device, for facilitating communication between the sensor 12 and various types of monitors, including older or newer versions of the patient monitor 20 or other physiological monitors. The cable 46 may be permanently coupled to the sensor 12, or it may be removably coupled to the sensor 12—the latter alternative being more useful and cost efficient in situations where the sensor 12 is disposable.

As will be appreciated by those of ordinary skill in the art, the sensor cable 46 is typically used to transmit control or timing signals from the monitor 20 to the sensor 12 and/or to transmit acquired data from the sensor 12 to the monitor 20. In other embodiments, the sensor 12 and the patient monitor 20 may communicate via wireless means, such as using radio, infrared, or optical signals. In such embodiments, a transmission device (not shown) may be connected to the sensor 12 to facilitate wireless transmission between the sensor 12 and the patient monitor 20.

In one embodiment, the patient monitor 20 may be a suitable pulse oximeter, such as those available from Nellcor Puritan Bennett Inc. In other embodiments, the patient monitor 20 may be a monitor suitable for measuring tissue hydration, glucose levels, or other blood or tissue related metrics, using spectrophotometric or other techniques. Furthermore, the monitor 20 may be a multi-purpose monitor suitable for performing pulse oximetry and measurement of tissue hydration, or other combinations of physiological and/or biochemical monitoring processes, using data acquired via the sensor 12. Furthermore, to supplement the monitoring functions provided by the monitor 20, the monitor 20 may be coupled to a multi-parameter patient monitor 48 via a cable 50 connected to a sensor input port and/or via a cable 52 connected to a digital communication port.

Figure 3:
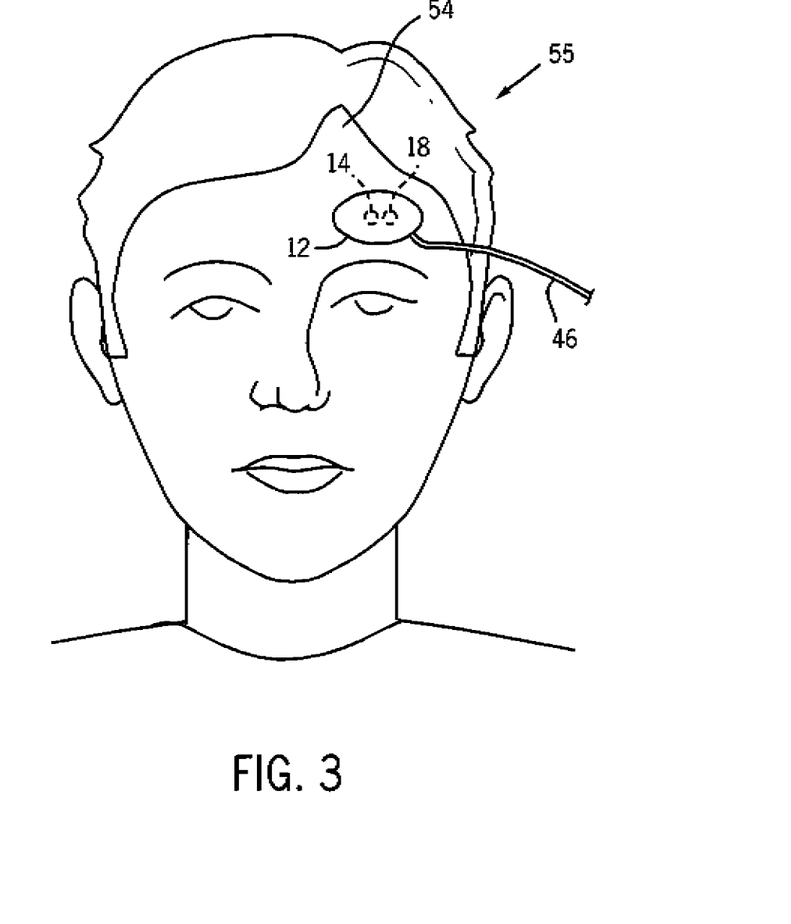
FIG. 3 illustrates the reflectance-type forehead patient sensor of FIG. 2 in use on a patient's forehead, in accordance with aspects of the present technique.

The exemplary sensor 12 depicted in FIGS. 1-3 includes an emitter 14 and a detector 18, as discussed with regard to FIG. 1, which may be of any suitable type. For example, the emitter 14 may be one or more light emitting diodes adapted to transmit one or more wavelengths of light, such as in the red to infrared range, and the detector 18 may be one or more photodetectors, such as a silicon photodiode package, selected to receive light in the range emitted from the emitter 14. The type and number of detectors 24 present in the sensor 12 may depend on how many and what wavelengths are emitted by the emitter 14.

The exemplary sensor 12 described with regard to FIGS. 1-3 is depicted as a reflectance-type sensor for use in pulse oximetry or other spectrophotometric applications, though in some embodiments of the present technique it may instead be configured for use as a transmission-type sensor. Transmission-type sensors include an emitter 14 and detector 18 that are typically placed on opposing sides of the sensor site. During operation, the emitter shines one or more wavelengths of light through the patient's fingertip or other tissue, and the light received by the detector is processed to determine the desired physiological characteristics of the patient.

Reflectance-type sensors include an emitter 14 and detector 18 that are typically placed on the same side of the sensor site, as generally depicted with regard to FIGS. 1-3. During operation, the emitter shines one or more wavelengths of light into the patient's tissue. A certain amount of the light is eventually reflected back toward the tissue surface where it is detected by the detector and processed to determine the desired physiological characteristics of the patient. For simplicity, the exemplary embodiment of the sensor 12 described herein is adapted for use as a reflectance-type sensor. As will be appreciated by those of ordinary skill in the art, however, such discussion is merely exemplary and is not intended to limit the scope of the present technique.

For pulse oximetry applications using either transmission or reflectance type sensors, the oxygen saturation of the patient's arterial blood may be determined using two or more wavelengths of light, most commonly red and near infrared wavelengths. Similarly, in other applications, tissue hydration (or other body fluid related metric) or a concentration of one or more biochemical components in an aqueous environment may be measured using two or more wavelengths of light, most commonly near infrared wavelengths between about 1,000 nanometers to about 2,500 nanometers. It should be understood that, as used herein, the term "light" may refer to one or more of radio wave, millimeter wave, microwave, infrared, visible, ultraviolet, or even X-ray electromagnetic radiation, and may also include any wavelength within the radio wave, millimeter wave, microwave, infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. Common pulse oximetry sensor sites include a patient's fingertips, toes, forehead, or earlobes. Regardless of the placement of the sensor 12, the reliability of the spectrophotometric measurement is related to the accurate detection of transmitted or reflected light that has passed through the patient's tissue and has not been inappropriately supplemented by outside light sources or modulated by subdermal anatomic structures. Such inappropriate supplementation and/or modulation of the light emitted by the sensor 12 can cause variability in the resulting spectrophotometric measurements. Therefore, to ensure accurate detection of the transmitted or reflected light, the sensor 12 should remain in contact with the patient's tissue. Failure to do so can result in inaccurate measurement of the desired physiological characteristics.

Another factor that may affect the sensor's reliability is the occurrence of light shunting. As discussed above, the accurate detection of transmitted or reflected light is related to the reliability of the pulse oximetry measurement. Light shunting occurs when light emitted from the emitter 14 in the sensor 12 arrives at the detector 18 without first having traveled through the patient's tissue. The light shunting may cause measurement variations that do not relate to the amount of blood or tissue constituent and, therefore, may lead to inaccurate measurements. Light shunting may be minimized by ensuring adequate contact between the sensor 12 and the patient's tissue. However, in the event light shunting occurs, the effects of light shunting may be corrected using the techniques described herein.

Turning now to FIG. 3, the exemplary reflectance-type sensor 12 is shown fitted to the forehead 54 of a patient 55.

Further, as discussed above, the sensor 12 is connected to the monitor 20 by a sensor cable 46. The physical connection of the sensor 12 to the monitor 20 by the sensor cable 46 and the mechanism of attachment to the forehead 54 (such as adhesives, bandages, and so forth) may cause or allow the sensor 12 to be moved relative to the measurement site, i.e., forehead 54, due to incidental motion of the patient 55 or of nearby medical personnel. Additionally, the sensor 12 may be mistakenly removed by the patient 55 or medical personnel. The present technique provides exemplary acts to determine if the sensor 12 is in suitable contact with the patient's tissue, such as the patient's forehead 54.

As noted above, for spectrophotometric applications measuring blood or tissue constituent levels, contact between the sensor 12 and the intended tissue bed is important. In one embodiment of the present technique, the presence of water, which is an abundant component of virtually all tissue beds to which an optical sensor is typically applied, is used to determine whether the sensor 12 is in suitable contact with the tissue. In such an embodiment, the emitter 14 emits light at a wavelength at which water is generally opaque, so that light emitted at the wavelength is generally not reflected through the tissue when the sensor is in suitable contact with the tissue. Typically the light emitted at the water-opaque wavelength is in addition to the wavelengths employed for measuring the physiological characteristic of interest, such as blood oxygen saturation.

In such an embodiment, suitable contact between the sensor 12 and the tissue may be indicated by the general absence of light at the water-opaque wavelength at the detector 18 due to the absorption of light at that wavelength by the tissue. Conversely, insufficient contact between the sensor 12 and the tissue may be indicated by an unexpectedly high measurement of light at the water-opaque wavelength at the detector 18. For example, in a situation where the sensor 12 is in poor contact with the tissue, an unexpectedly high measurement of light at the water-opaque wavelength may be observed at the detector 18 (such as due to reflection of the light off of the tissue surface or multiple reflections between the tissue surface and the sensor interior) compared to a situation where the sensor 12 is in good contact with the tissue.

A typical water absorption band used in an exemplary sensor embodiment is between about 1,200 nanometers to about 1,600 nanometers, but additional wavelengths and absorption bands may also be used. The wavelengths of the emitted light may be selected based upon the absorption bands of any desired blood or tissue constituents. Further, the absorption band, and therefore the choice of light sources in the emitter 14, may be chosen based upon the expected or average optical path length, i.e. the distance between the emitter 14 and the detector 18, when the sensor 12 is positioned on a patient.

For example, an emitter 14 may emit light at a water-opaque wavelength between about 1,400 nanometers to about 1,600 nanometers in an implementation where the emitter 14 and detector 18 are separated by about 2.5 mm to about 4.5 mm. In other embodiments, the light emitted at the additional water-opaque wavelength may be in the wavelength range between about 1,200 nanometers to about 1,400 nanometers or between about 1,870 nanometers to about 2,000 nanometers. For example, in implementations where the emitter 14 and detector 18 are about 10 mm apart from one another (as is typically observed where transmission-type oximetry sensors are employed on a finger), the additional water-opaque wavelength may be between about 1,200 nanometers to about 1,400 nanometers. Light in this wavelength range is more penetrating of water and is, therefore, more likely to be detectable across the greater optical path length.

As will be appreciated by those of ordinary skill in the art, selection of a suitable wavelength for the additional wavelength may be based upon the desired amount of detectable signal at the detector 18, the tissue constituent (such as water) which is to be generally opaque to the light, and/or the expected optical path length. Longer, less penetrating wavelengths may be chosen based on a combination of the opacity of water, the optically dominant blood or tissue component, and the expected optical path length. For example, a longer wavelength may be used when less penetration of the tissue at the sensor site is desired, such as in embodiments where a reflectance-type sensor 12 is used on the forehead such that the emitter and detector have a relatively short optical path length.

The preceding examples relate to the use of water as the tissue constituent used to assess sensor placement. However, one of ordinary skill in the art will recognize that water is only one example and that virtually any tissue constituent may be utilized if the constituent is present in sufficient quantities at the sensor site so as to absorb light and if a suitable wavelength can be identified for which the constituent is substantially opaque. For example, hemoglobin and/or myoglobin may be satisfactory tissue constituents for use in accordance with the present technique as they are present throughout the body and have the desired optical traits. In this example, a wavelength in the range of about 500 nm to about 600 nm, where hemoglobin or myoglobin may be the dominant optical absorbers, may be used to verify that a sensor 12 is in contact with tissue containing adequate quantities of these analytes.

The preceding discussion has related examples of tissue constituents that may be employed in accordance with the present technique and exemplary wavelengths that may be absorbed by these constituents. The use of these wavelengths in assessing sensor contact is now discussed. For example, in one implementation water is the tissue constituent of interest and light is emitted by the sensor 12 at a water-opaque wavelength of about 1,480 nanometers. In this implementation, when the sensor 12 is in suitable contact with the patient 16, the amount of light measured by the detector 18 at this water-opaque wavelength is less than or equal to about two percent of a reference intensity measurement taken using a water-free substance at the same light wavelength. In other words, in such an implementation, the reference intensity measurement at the same wavelength in the absence of water is fifty times the intensity of the light detected when the sensor 12 is in sufficient contact with the tissue. Therefore, in such an implementation with suitable sensor-tissue contact, the water within the intervening tissue between the emitter 14 and detector 18 absorbed approximately ninety-eight percent or more of the emitted light having a wavelength of 1,480 nanometers relative to a comparable water-free volume. However, for sensor placements where the sensor 12 is not in good contact with the tissue, the amount of light at 1,480 nanometers reaching the detector 18 may be roughly ten times greater than the amount of light reaching the detector when there is sufficient sensor contact. In other words, the intensity of light at the water-opaque wavelength is 20% of the reference intensity of light at the same wavelength measured in a comparable water-free volume.

Thus, in such an implementation, observation of an unexpectedly high amount of light at a water-opaque frequency, such as 1,480 nanometers, may be used to determine the sufficiency of sensor-tissue contact. For example, the amount of light detected by the detector 18 at the water-opaque wavelength (assuming water is the tissue constituent being assessed) may be compared to a threshold value to determine sensor contact sufficiency. For example, such a threshold may be empirically set according to the observations described above, i.e., as a ratio or multiple of the intensity of the detected light at the water-opaque wavelength to a reference intensity measurement taken from a water-free substance at the same water-opaque wavelength. In one such example, a threshold is set such that light detected at the water-opaque wavelength that is greater than or equal to 20% of a reference intensity measurement at that same wavelength may indicate that the sensor 12 is not in good contact with the tissue of the patient 16. Other ratios, such as 30%, 40%, 50%, and so forth, may be employed. As will be appreciated, the selection of the threshold, whether selected empirically or as a fraction or ratio of a reference intensity measurement, will generally determine the sensitivity of the system in assessing the sufficiency of sensor placement and may be selected based on the desired sensitivity. Any fraction or ratio up to or including 100% of a reference intensity measurement may be used depending on the desired sensitivity of the system. Other factors that may be considered in establishing the threshold include the risk tolerance for false-positive and false-negative results and/or the time sensitivity between when a sensor 12 begins to lose sufficient contact and when a notification is provided.

As will be appreciated, thresholds based on the reference intensity measurements taken using a water-free substance may be generated before and/or during the monitoring session. Alternatively, the thresholds may be stored in a memory component, such as encoder 40, ROM 26, and/or RAM 28, of the sensor 12, the monitor 20 or 48, and/or the cable 46. In such an implementation, the thresholds may be stored in the memory component at the time of manufacture of the respective component or after manufacture, such as at the time of first use of the sensor 12. In addition, the thresholds stored in the memory component may be updated, if desired, at subsequent fixed time or usage intervals.

In another embodiment, the threshold may not be determined from an intensity measurement of a water-free substance at the same water-opaque wavelength as described above. For example, the amount of light at a water-opaque wavelength reaching the detector 18 may instead be compared to the amount of light at a different reference wavelength reaching the detector 18. In such an implementation, the reference wavelength may be less opaque, i.e., more penetrating, relative to water and may be measured concurrently or alternatingly on the same tissue as the water-opaque wavelength of light. In one such embodiment, the reference wavelength may be one of the wavelengths employed in measurement of physiological characteristics using the sensor 12, such as a red or near infrared wavelength. In this manner, the ratio of the intensity of the detected light at the water-opaque wavelength relative to the intensity of the detected light at the reference wavelength provides an indication of the quality of sensor contact with the patient's tissue. For example, if the sensor 12 is in good contact with the patient's tissue, the intensity of the detected light at the water-opaque wavelength may only be two percent of the intensity of the detected light at a red or near infrared wavelength that has been absorbed and reflected back to the detector 18. If, however, the sensor is not in good contact with the patient's tissue, most of the light at the water-opaque wavelength will not be absorbed by the water in the patient's tissue and may instead be reflected to the detector 18. In this case the ratio of the intensity of the detected light at the water-opaque wavelength to the intensity of the detected light at the reference red or near infrared wavelengths will be much greater.

As a result, an amount of light detected at the water-opaque wavelength that is too high relative to the light detected at a reference visible or infrared wavelength may be used as a threshold. For example, if the amount of light detected at the water-opaque wavelength is expected (such as due to empirical analysis or experience) to be 5% of the light detected at a reference wavelength, a threshold may be established at the expected ratio, i.e., 5%, or at some value greater than the expected ratio, such as 8%, 10%, 15%, and so forth. In this manner, thresholds based on a reference wavelength may be established that take time sensitivity and/or risk sensitivity to false-negative and false-positive readings into account. As will be appreciated, though use of a single visible or infrared reference wavelength has been discussed for simplicity, more than one reference wavelength may be employed in assessing sensor contact sufficiency.

For example, in a pulse oximetry context, two additional wavelengths of light may be used in assessing the physiological characteristics of interest. In such an implementation, one or both of the physiological wavelengths may be employed in assessing sensor contact. For example, a separate threshold may be employed relative to each physiological wavelength or a single threshold may be employed based on the aggregate light intensity for the combined physiological wavelengths. As will be appreciated, in contexts where multiple reference wavelengths are employed, the comparisons, and related determinations of sensor contact sufficiency, may be independent of one another, i.e., the light detected at the water-opaque wavelength may be separately and independently compared to each reference wavelength. Alternatively, the comparisons may be combined, i.e., both thresholds must be exceeded to generate an indication that the sensor contact is insufficient, or may be hierarchical in nature, i.e., the threshold associated with the second reference wavelength is checked only after the threshold associated with the first reference wavelength is exceeded. While the preceding examples have related to the use of water as the tissue constituent and of corresponding water-opaque wavelengths, as noted previously, other constituents such as hemoglobin or myoglobin may also be employed along with suitable wavelengths of light that are absorbed by the selected tissue constituent.

Figure 4:
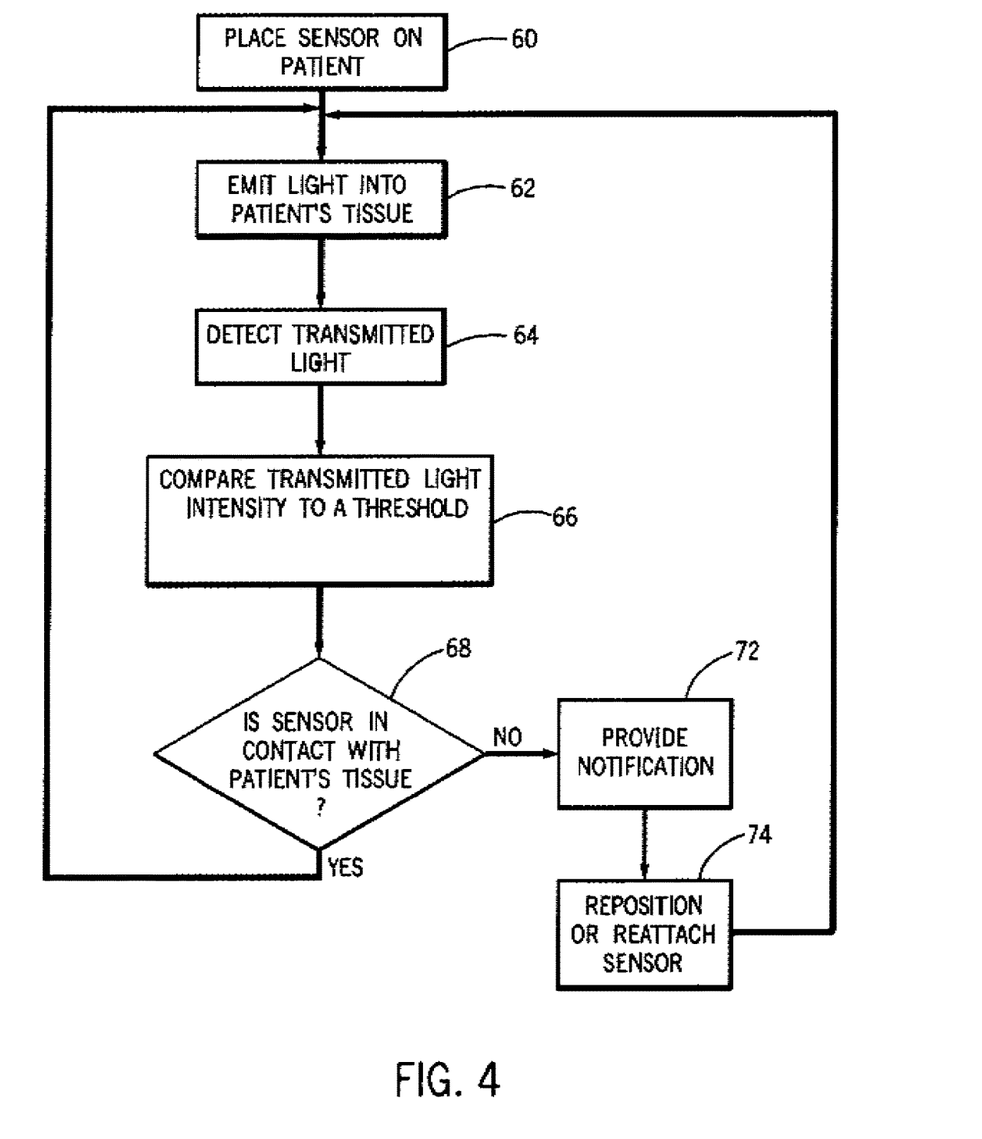
FIG. 4 is a flowchart depicting exemplary actions for determining contact of a sensor with a patient's tissue, in accordance with the present technique.

With the preceding discussion in mind and referring now to FIG. 4, exemplary acts for determining contact between a sensor 12 and a patient's tissue in accordance with the present technique are depicted. The acts described in FIG. 4 may be performed with any configuration of sensor, i.e., transmission or reflectance sensors, and with different types of spectrophotometric monitoring systems, such as systems for measuring blood oxygen saturation or tissue hydration. For simplicity, however, the actions described with relation to FIG. 4 are discussed with reference to an exemplary pulse oximetry implementation.

Turning now to FIG. 4, the sensor 12 is placed on the patient (block 60), such as attached onto a patient's forehead 54. The emitter 14 emits light into the patient's tissue (block 62). In addition to the red and near infrared wavelengths used for pulse oximetry, a third wavelength of light is also emitted which is different from those used in deriving pulse oximetry measurements. As discussed above, the third wavelength of light is absorbed by various blood or tissue constituents, such as water, myoglobin, or hemoglobin. In one pulse oximetry embodiment, the third wavelength is in the range of about 1,200 nanometers to about 1,400 nanometers, i.e. a water-opaque wavelength. The reflected light from the emitter is received by the detector (block 64) after absorption by blood and tissue constituents. The intensity of the light detected at the third wavelength is compared to a reference intensity measurement or wavelength (block 66), as described above. Based upon the comparison between the intensity of the reflected light of the third wavelength and the reference, the quality of the contact between the sensor and the patient's tissue may be determined (block 68).

If the ratio of the intensity of the reflected light to the reference intensity is below a threshold value, then the sensor is determined to be in contact with the patient's tissue. For example, in one embodiment, the intensity of the reflected light at the exemplary wavelength should be approximately two percent or less of the reference intensity when the sensor 12 is in good contact with the patient, i.e., the threshold value is two percent. Conversely, in this example, if the ratio of the intensity of the reflected light to the reference intensity is above the threshold value, the sensor is determined to not be in adequate contact with the patient's tissue. For example, in various respective embodiments, if the intensity of the reflected light at the exemplary water-opaque wavelength is more than 20%, 40%, or 50% greater than the intensity of the reflected light at sufficient sensor contact, the sensor 12 is determined to have poor contact with the patient's tissue.

If the sensor is determined to be in good contact with the patient's tissue, monitoring continues and no notification (or a positive indication of suitable contact) is provided to a technician or clinician. If the sensor is determined not to be in good contact with the patient's tissue, a notification is provided to the technician or clinician (block 72). The notification may be audio, visual, or both, and may be displayed on the sensor 12, patient monitor 20, or multiparameter monitor 48. Following this notification, the operator may attempt to reattach or reposition the sensor (block 74) to achieve suitable sensor contact. Once the sensor is repositioned or reattached, monitoring may be resumed.

In other embodiments of the present technique, a measure of light shunting may be determined instead of or in addition to an indication of sensor contact. For example, turning to FIG. 5, exemplary acts for determining the amount of light shunting in accordance with the present technique are depicted. The acts described in FIG. 5 may be performed in any configuration of the sensor and monitor system, including transmission and reflectance sensors and measurement of different physiological characteristics such as blood oxygen saturation or tissue hydration. For the purpose of illustration, an exemplary pulse oximetry implementation will be described, though other monitoring applications are also encompassed.

Figure 5:
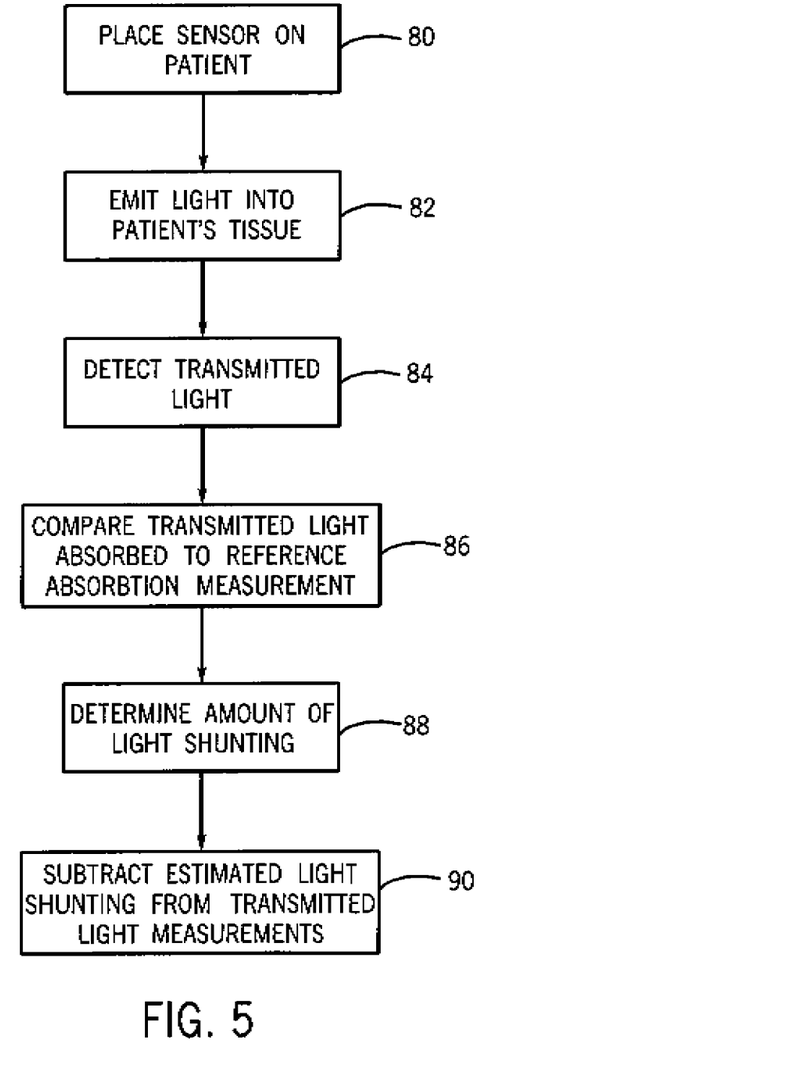
FIG. 5 is a flowchart depicting exemplary actions for correcting light shunting in a sensor, in accordance with the present technique.

The sensor is first placed on the patient (block 80), such as attached onto a patient's forehead 54 using a suitable sensor 12 as described above. The emitter 14 emits light into the patient's tissue (block 82). In addition to the red and near infrared wavelengths used for pulse oximetry, a third wavelength of light is also emitted which is different from those used in deriving pulse oximetry measurements. As discussed above, in one embodiment, the third wavelength is in the range of about 1,200 nanometers to about 1,400 nanometers, i.e. a water-opaque wavelength. The reflected light of the third wavelength is received by the detector (block 84) after absorption by blood and tissue constituents. The percentage of reflected light of the third wavelength received at the detector 18 is compared to a reference value (block 86). In one embodiment, the reference value is the intensity of reflected light absorbed under normal conditions, i.e. with no light shunting. The reference value may be the intensity of reflected light at the same wavelength in the absence of shunting or the reference value may be taken at a different wavelength with a known absorption relationship to the third wavelength. From this comparison, the amount of light shunting is determined (block 88).

For example, the observed reflected light at the third wavelength may be approximately 99.2% absorbed and the normal absorption as determined by the reference absorption measurement may be approximately 99.8%. The difference between the two percentages corresponds to the amount of light shunting occurring during operation of the sensor under the present conditions. The estimated amount of light shunting can be subtracted or otherwise compensated for in the reflected light measurements at other wavelengths (block 90), such as the reflected light measurements received in the red and near infrared wavelengths used in a pulse oximetry sensor. For example, the light shunting at the exemplary water-opaque wavelength may be proportional to the light shunting at the visible or infrared wavelengths in a one-to-one relationship or in some other empirically determined scaled relationship. The desired physiological characteristics, such as blood oxygen saturation, can be determined from the reflected light measurement at the other wavelengths emitted by the sensor corrected for the amount of light shunting observed at the third wavelength. Those skilled in the art will appreciate that subtracting or otherwise compensating for shunted light at these other wavelengths may involve rescaling the measured shunt at the third wavelength, based on factors such as emitter or detector efficiency or the optical reflective properties of skin or of the sensor interior.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission-type sensors for use in pulse oximetry, but also to reflectance-type sensors and other sensor designs as well. Likewise, the present techniques are not limited to use on fingers and toes but may also be applied to placement on other body parts such as in embodiments configured for use on the ears, nose, or forehead.

What is claimed is:

1. A method for correcting light shunting, comprising:
    emitting light at three or more wavelengths from at least one emitter of a sensor into a patient's tissue, wherein the three or more wavelengths includes a first wavelength that is not used to determine a physiological characteristic of the patient;
    detecting the light with at least one detector of the sensor;
    comparing the intensity of the detected light at the first wavelength to a threshold;
    determining the amount of light shunting between the at least one emitter and the at least one detector based on the comparison; and
    processing the detected light at one or more of a second wavelength or a third wavelength to compensate for the amount of light shunting.

2. The method of claim 1, wherein processing the detected light comprises comprising correcting the intensity of the detected light at one or more of the second wavelength or the third wavelength based on the amount of light shunting.

3. The method of claim 2, wherein correcting the intensity comprises subtracting the amount of light shunting from the intensity of the detected light at the second wavelength or the third wavelength.

4. The method of claim 2, comprising determining a physiological characteristic based upon the corrected intensity of the detected light at the second or third wavelengths.

5. The method of claim 1, wherein comparing the intensity comprises comparing a ratio of the intensity of the detected light at the first wavelength to a reference intensity of light at the first wavelength to the threshold.

6. The method of claim 1, wherein comparing the intensity comprises comparing a ratio of the intensity of the detected light at the first wavelength to a reference intensity of light at a different wavelength to the threshold.

7. The method of claim 1, wherein the first wavelength is primarily absorbed by water.

8. The method of claim 7, wherein the first wavelength of the detected light is between about 1200 nanometers to about 1600 nanometers.

9. The method of claim 1, wherein the sensor comprises a sensor configured to measure tissue hydration.

10. The method of claim 1, wherein the sensor comprises a pulse oximetry sensor.

11. The method of claim 1, determining if the sensor is in contact with the patient's tissue based on the comparison.

12. A patient monitor, comprising:
a port configured to connect to a sensor; and
a processor configured to receive signals from the port and to use the signals when executing an algorithm configured to compare an intensity of a first wavelength of detected light to a threshold, wherein the first wavelength is not used to determine a physiological characteristic of a patient, and wherein the processor is also configured to execute a second algorithm configured to determine an amount of light shunting between at least one emitter of the sensor and at least one detector of the sensor based on the comparison, and wherein the processor is configured to process the signals related to one or more other wavelengths of detected light to compensate for the amount of light shunting.

13. The patient monitor of claim 12, wherein the algorithm comparing the intensity is configured, when executed by the processor, to compare a ratio of the intensity of the first wavelength of the detected light to a reference intensity of light at the first wavelength to the threshold.

14. The patient monitor of claim 12, wherein the algorithm comparing the intensity is configured, when executed by the processor, to compare a ratio of the intensity of the first wavelength of the detected light to a reference intensity of light at a different wavelength to the threshold.

15. The patient monitor of claim 12, wherein the first wavelength is configured to be primarily absorbed by water.

16. The patient monitor of claim 12, wherein the first wavelength is configured to be primarily absorbed by myoglobin or hemoglobin.

17. The patient monitor of claim 12, wherein the processor is configured to execute a third algorithm to determine if the sensor is in contact with the patient's tissue based on the comparison.

18. A patient monitoring system, comprising:
a sensor comprising:
an emitter configured to emit light at three or more wavelengths into a patient's tissue; and
a detector configured to detect the light; and
a monitor configured to execute an algorithm configured to compare an intensity of a wavelength of detected light to a threshold, wherein the wavelength is not used to determine a physiological characteristic of the patient, and a second algorithm configured to determine an amount of light shunting between the emitter and the detector based on the comparison, and to process the detected light at one or more other wavelengths of the three or more wavelengths to compensate for the amount of light shunting.

19. The patient monitoring system of claim 18, wherein the algorithm comparing the intensity is configured, when executed by the monitor, to compare a ratio of the intensity of the wavelength of the detected light a reference intensity of light at the wavelength to the threshold.

20. The patient monitoring system of claim 18, wherein the algorithm comparing the intensity is configured, when executed by the monitor, to compare a ratio of the intensity of the wavelength of the detected light to a reference intensity of light at a different wavelength to the threshold.

* * * * *